United States Patent
Schwabacher et al.

(10) Patent No.: US 7,244,572 B1
(45) Date of Patent: Jul. 17, 2007

(54) ONE-DIMENSIONAL ARRAYS ON OPTICAL FIBERS

(75) Inventors: Alan W. Schwabacher, Shorewood, WI (US); Peter Geissinger, Shorewood, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 0 days.

(21) Appl. No.: 09/535,300

(22) Filed: Mar. 24, 2000

(51) Int. Cl.
*G01N 33/53* (2006.01)
*C12M 1/34* (2006.01)

(52) U.S. Cl. .................. 435/7.1; 435/4; 435/287.1; 435/288.7; 435/DIG. 2; 435/DIG. 15; 435/DIG. 43; 435/DIG. 45

(58) Field of Classification Search .............. 435/4, 435/7.1, 287.1, 288.1, 808, 288.7, DIG. 2, 435/DIG. 15, DIG. 43, DIG. 45; 436/8, 436/578, 524, 527, 164, 172, 805; 422/57, 422/82.11; 530/300, 333, 334
See application file for complete search history.

(56) References Cited

U.S. PATENT DOCUMENTS

| | | | |
|---|---|---|---|
| 4,689,405 A | 8/1987 | Frank et al. ................ 536/27 |
| 4,848,687 A * | 7/1989 | Myers et al. ............ 242/474.9 |
| 5,030,841 A | 7/1991 | Wampfler ................... 250/571 |
| 5,143,854 A | 9/1992 | Pirrung et al. ............. 436/518 |
| 5,445,934 A | 8/1995 | Fodor et al. .................. 435/6 |
| 5,510,270 A | 4/1996 | Fodor et al. ............... 436/518 |
| 5,527,681 A | 6/1996 | Holmes ........................ 435/6 |
| 5,547,839 A | 8/1996 | Dower et al. ................. 435/6 |
| 5,565,324 A | 10/1996 | Still et al. ................... 435/6 |
| 5,585,275 A | 12/1996 | Hudson et al. ............ 436/518 |
| 5,599,695 A | 2/1997 | Pease et al. ............... 435/91.1 |
| 5,688,696 A | 11/1997 | Lebl .......................... 436/518 |
| 5,807,754 A | 9/1998 | Zambias et al. ........... 436/518 |
| 5,837,196 A | 11/1998 | Pinkel et al. ............... 422/55 |
| 6,037,186 A * | 3/2000 | Stimpson ................... 436/518 |
| 6,040,191 A * | 3/2000 | Grow ......................... 436/172 |
| 6,156,494 A * | 12/2000 | Adams et al. ................ 435/4 |

FOREIGN PATENT DOCUMENTS

| EP | 0 385 433 | 9/1990 |
| WO | WO 96/16078 | 5/1996 |
| WO | WO 99/42605 | 8/1999 |

OTHER PUBLICATIONS

Arkles, "Tailoring Surfaces With Silanes" *Chemtech* 7:766-778, 1977.

Blair et al., "Study of Analyte Diffusion into a Silicone-Clad Fiber-Optic Chemical Sensor by Evanescent Wave Spectroscopy" *Appl. Spectr.* 49:1636-1645, 1995.

Brenner et al., "Encoded combinatorial chemistry" *Proc. Natl. Acad. Sci. USA* 89:5381-5383, 1992.

Briceño et al., "A Class of Cobalt Oxide Magnetoresistance Materials Discovered with Combinatorial Synthesis" *Science* 270:273-275, 1995.

Browne et al., "Intrinsic Sol-Gel Clad Fiber-Optic Sensors with Time-Resolved Detection" *Analytical Chemistry* 68:2289-2295, 1996.

Bunin et al., "The Combinatorial Synthesis and Chemical and Biological Evaluation of a 1,4-Benzodiazepine Library" *Proc. Natl. Acad. Sci. USA* 91:4708-4712, 1994.

Colin et al., "The Effect of Mode Distribution on Evanescent Field Intensity: Applications in Optical Fiber Sensors" *Appl. Spectrosc.* 45:1291-1295, 1991.

Colin et al., "The Effect of Length and Diameter on the Signal-to-Noise Ratio of Evansecent Field Absorption Fiber-Optic Sensors" *Appl. Spectrosc.* 46:1129-1133, 1992.

Czarnik, "Encoding strategies in Combinatorial chemistry" *Proc. Natl. Acad. Sci. USA* 94:12738-12739, 1997.

Czarnik, "Encoding methods for Combinatorial chemistry" *Current Opinion in Chemical Biology* 1:60-66, 1997.

Danielson et al., "A combinatorial approach to the discovery and optimization of luminescent materials" *Nature* 389:944-948, 1997.

DeWitt et al., "Diversomer™ Technology: Solid Phase Synthesis, Automation, and Integration for the Generation of Chemical Diversity" *Drug Development Research* 33:116-124, 1994.

Devlin et al., "Random Peptide Libraries: A Source of Specific Protein Binding Molecules" *Science* 249:404-406, 1990.

(Continued)

*Primary Examiner*—Mark L. Shibuya
(74) *Attorney, Agent, or Firm*—Choate, Hall & Stewart; Brenda Herschbach Jarrell; C. Hunter Baker

(57) ABSTRACT

Linear arrays of chemosensors or chemical compounds are supported by an optical fiber that allows one to rapidly assay the entire array using changes in optical properties such as fluorescence. The location of the agent along the fiber determines the identity of the agent in these linear arrays. Combinatorial libraries may be constructed on the fiber as well as assayed on the optical fiber. A system and method of analyzing the entire array of agents on an optical fiber using a light source, an optical fiber, and a detector are also described. The time delay between the excitation and detection determines the location being assayed along the fiber and therefore the identity of the agent being assayed. The present invention may find uses in the medical, pharmaceutical, environmental, defense, and food industries.

16 Claims, 12 Drawing Sheets

OTHER PUBLICATIONS

Egami et al., "Evanescent Wave Spectroscopic Fiber Optic pH Sensor" *Opt. Communc.* 122:122-126, 1996.

Fodor, *Faseb J.* 11:A879, 1997. Abstract 121.

Fodor, "Massively Parallel Genomics" *Science* 277:393-395, 1997.

Fodor et al, "Light-Directed, Spatially Addressable Parallel Chemical Synthesis" *Science* 251:767-773, 1991.

Frank et al., "Spot-Synthesis: An Easy Technique for the Positionally Addressable, Parallel Chemical Synthesis on a Membrane Support" *Tetrahedron* 48(42):9217-9232, 1992.

Freier et al., "Deconvolution of Combinatorial Libraries for Drug Discovery: A Model System" *J. Med. Chem.* 38:344-352, 1995.

Furka et al, "General method for rapid synthesis of multicomponent peptide mixtures" *Int. J. Peptide Protein Res.* 37:487-493, 1991.

Furka et al., "String Synthesis. A Spatially Addressable Split Procedure" *J. Comb. Chem.* 2(3): 220-223, 2000.

Ge et al. "Fiber-Optic pH Sensor Based on Evanescent Wave Absorption Spectroscopy" *Anal. Chem.* 65:2335-2338, 1993.

Gennari et al., *Liebigs Ann./Recueil.* 637-647, 1997.

Geysen et al., "*A priori* Delineation of a Peptide Which Mimics a Discontinuous Antigenic Determinant" *Mol. Immun.* 23(7):709-715, 1986.

Gravert et al., "Organic Synthesis on Soluble Polymer Supports: Liquid-Phase Methodologies" *Chem. Rev.* 97:489-509, 1997.

Gupta et al., "Fiber-Optic Evanescent Field Absorption Sensor: A Theoretical Evaluation" *Fiber Integrated Opt.* 13:443-443, 1994.

Gupta et al., "Experimental Studies on the Response of the Fiber Optic Evanescent Field Absorption Sensor" *Fiber and Integrated Optics* 17:63-73, 1998.

Houghten et al., "Generation and use of synthetic peptide combinatorial libraries for basic research and drug discovery" *Nature* 354:84-86, 1991.

Konings et al., "Deconvolution of Combinatorial Libraries for Drug Discovery: Theorectical Comparison of Pooling Strategies" *J. Med. Chem.* 39:2710-2719, 1996.

Krchňák et al., "Noninvasive Continuous Monitoring of Solid-Phase Peptide Synthesis by Acid-Base Indicator" *Collect. Czech. Chem. Commun.* 53:2452-2548, 1988.

Kricka, "Selected Strategies for Improving Sensitivity and Reliability of Immunoassays" *Clin. Chem.* 40(3):347-357, 1994.

Lam et al., "A new type of synthetic peptide library for identifying ligand-binding activity" *Nature* 354:82-84, 1991.

Lam et al., "The 'One-Bead-One-Compound' Combinatorial Library Method" *Chem. Rev.* 97:411-448, 1997.

Liang et al., "Parallel Synthesis and Screening of a Solid Phase Carbohydrate Library" *Science* 274:1520-1522, 1996.

MacBeath et al., "Printing Small Molecules as Microarrays and Detecting Protein-Ligand Interactions en Masse" *J. Am. Chem. Soc.* 121:7967-7968, 1999.

Marcuse, "Launching Light into Fiber Cores from Sources Located in the Cladding" *J. Lightwave Technolog.* 6(8) :1273-1279, 1988.

Messica et al., "Theory of Fiber-Optic, Evanescent-Wave Spectroscopy and Sensors" *Appl. Opt.* 35:2274-2284, 1996.

Michael et al. "Randomly Ordered Addressable High-Density Optical Sensor Arrays" *Analytical Chemistry* 70:1242-1248, 1998.

Nefzi et al., "The Current Status of Heterocyclic Combinatorial Libraries" *Chem Rev.* 97:449-472, 1997.

Ohlmeyer et al., "Complex synthetic chemical libraries indexed with molecular tags" *Proc. Natl. Acad. Sci. USA* 90:10922-10926, 1993.

Pilevar et al., "Tapered Optical Fiber Sensor Using Near-Infrared Fluorophores to Assay Hybridization" *Anal. Chem.* 70:2031-2037, 1998.

Pirrung, "Spatially Addressable Combinatorial Libraries" *Chem. Rev.* 97:473-488, 1997.

Radhakrishnan et al. "Fiber Optic Sensor Based on Evanescent Wave Absorption" *Opt. Eng.* 32:692-694, 1993.

Reddington et al., "Combinatorial Electrochemistry: A Highly Parallel, Optical Screening Methods for Discovery of Better Electrocatalysts" *Science* 280:1735-1737, 1998.

Sapolsky et al., *Genetic Analysis: Biomolecular Engineering* 14:187-192, 1999.

Schmidt et al., "Molecular Interaction Between the *Strep*—tag Affinity Peptide and its Cognate Target, Streptavidin" *J. Mol. Biol.* 255:753-766, 1996.

Schwabacher et al., "Fourier Transform Combinatorial Chemistry" *J. Am. Chem. Soc.* 121(37):8669-8670, 1999.

Senkan, "High-throughtput screening of solid-state catalyst libraries" *Nature* 394:350-353, 1998.

Smith et al, "Necklace-Coded Polymer-Supported Combinatorial Synthesis of 2-Arylaminobenzimidazoles" *J. Comb. Chem.* 1:368-370, 1999.

Thompson et al., "Synthesis and Applications of Small Molecule Libraries" *Chem. Rev.* 96:555-600, 1996.

Liu, et al., "A Fiber-Optic Evanescent Wave DNA Biosensor Based on Novel Molecular Beacons", *Anal Chem.* 71:5054-5059, 1999.

International Search Report issued for corresponding PCT applicatation PCT/US01/07915.

Henry, C., "Combinatorial Chemistry Gains a New Dimension", Chemistry & *Engineering News* Sep. 13, 1999, p. 9.

Thomas, "It's A Wrap", *New Scientist* Sep. 18, 1999, p. 14.

"All-in-one synthesis and evaluation," *Analytical Chemistry,* p. 789A, Dec. 1, 1999.

* cited by examiner

Leaky mode – refracted wave into cladding; energy lost from core to cladding.

Guided mode – no refraction, but evanescent tail into cladding; no energy lost from core unless absorbing species within decay range.

ONE-DIMENSIONAL ARRAYS ON OPTICAL FIBERS

GOVERNMENT SUPPORT

The work described herein was supported, in part, by grants from the National Science Foundation (CHE-9726030). The United States government may have certain rights in the invention.

PRIORITY INFORMATION

This application claims priority to the application U.S. Ser. No. 09/253,153, filed Feb. 19, 1999 now abandoned, which claims priority to provisional application U.S. Ser. No. 60/075,629, filed Feb. 21, 1998. Both of these application are incorporated herein by reference.

BACKGROUND OF THE INVENTION

Chemosensors are used in a wide variety of measurements, from assaying components of a bodily fluid in a doctor's office to locating explosives in an airport. Arrays of sensors are of great utility, as they allow the detection of a large number of different species, or the high fidelity recognition of analytes using a large number of sensors of low selectivity. Data from a large array of chemical sensors can be analyzed to detect the presence or activity of particular chemical compounds or functional groups. Two-dimensional arrays are currently being used as biosensors in the medical field to screen for genetic and viral diseases. Many of these arrays include thousands of polynucleotides of known gene sequences on a small chip to detect for specific genes which are turned on or off in a particular cell line (Sapolsky et al. *Genetic Analysis: Biomolecular Engineering* 14:187-192, 1999; Lockhart *Nature Medicine* 4:1235-1236, 1998; Fodor *FASEB J.* 11:A879, 1997; Fodor *Science* 277:393-395, 1997; each of which is incorporated herein by reference). However, as these chips become larger and larger, the readout of the chip becomes increasingly time-consuming and cost intensive, and more sophisticated instrumentation is required to analyze the array. Even today, the expense and complexity of reading a chip is beyond what can reasonably be used in a doctor's office.

Many chemosensors used today undergo a change in an optical property such as absorbance or fluorescence upon binding of a chemical compound. Therefore, optical fibers are ideally suited to carry light to and from such optical chemosensors. Optical fiber bundles with a sensor placed at the end of each fiber are currently being developed by Illumina, Inc.

Combinatorial Chemistry and Drug Discovery

Combinatorial chemistry is another area of research where a large number of chemical compounds must be analyzed. The techniques of combinatorial chemistry allow the synthesis of thousands to millions of chemical compounds which may subsequently be screened in the search for new pharmaceutical agents, new catalysts, new chemosensors, or other materials with desired properties (Geysen et al. *Molec. Immunol.* 23:709-715, 1986; Houghton et al. *Nature* 354:84-86, 1991; Frank *Tetrahedron* 48:9217-9232, 1992; Bunin et al. *Proc. Natl. Acad. Sci. USA* 91:4708-4712, 1994; Thompson et al. *Chem. Rev.* 96:555-600, 1996; Keating et al. *Chem. Rev.* 97:449-472, 1997; Gennari et al. *Liebigs Ann./Recueil* 637-647, 1997; Reddington et al. *Science* 280:1735-1737, 1998; each of which is incorporated herein by reference). Before the advent of combinatorial chemistry, potential compounds were typically identified by laborious extraction and screening of natural products or by intricate, single-molecule syntheses.

In the preparation of a combinatorial library of chemical compounds, thousands to millions of compounds are synthesized on a small scale. The process usually starts with a core structure having several sites for functionalization and derivatization. Each of these sites is reacted under a variety of conditions with known reagents to yield a large number of products. The library may be synthesized by various methods, including the split-and-pool method and the parallel synthesis method. The synthetic steps may take place in solution or on a solid phase support, as is more commonly used (Lam et al. *Chem. Rev.* 97:411448, 1997; Nefzi et al. *Chem. Rev.* 97:449-472, 1997; Gennari et al. *Liebigs Ann./Recueil* 637-647, 1997; Gravert et al. *Chem. Rev.* 97:489-509, 1997; Thompson et al. *Chem. Rev.* 96:555-600, 1996; *Accts. Chem. Res.* 29, 1996 (special issue on combinatorial chemistry); Pirrung et al. *Chem. Rev.* 97:473-488, 1997; Czarnik *Curr. Opin. Chem. Biol.* 1:60, 1997; each of which is incorporated herein by reference). The resulting library is then screened using a known assay to identify compounds with a desired activity. The structure of the identified compound can then be determined, for example by decoding information on a solid support (Czarnik *Proc. Natl. Acad. Sci. USA* 94:12738-12739, 1997; Brenner et al. *Proc. Natl. Acad. Sci. USA* 89:5381-5283, 1992; Ohlmeyer et al. *Proc. Natl. Acad. Sci. USA* 90:10922-10926, 1993; U.S. Pat. No. 5,565,324; each of which is incorporated herein by reference) or by determining the compound's position in a spatially addressable array (Fodor et al. *Science* 251:767-773, 1991; U.S. Pat. No. 5,143,854; U.S. Pat. No. 5,547,839; Geysen et al. *Molec. Immunol.* 23:709-715, 1986; Houghton et al. *Nature* 354:84-86, 1991; each of which is incorporated herein by reference). The identified compound may be used as a lead compound in the development of pharmaceutical agents. However, the synthesis and analysis of an entire library, which may contain millions of compounds, is very time consuming and costly, and full scale library analysis is rarely done.

A method and system allowing for fully parallel synthesis of a combinatorial library and full scale analysis of the library would be very useful in the search for new pharmaceutical agents and other compounds with a variety of properties.

SUMMARY OF THE INVENTION

The present invention provides a linear array of agents on an optical fiber. The agents may comprise chemical compounds, and may, for example, represent a combinatorial chemical library. The compounds may be synthesized and/or analyzed on the optical fiber. Preferably, any assay used to analyze the compounds involves a change in an optical property such as fluorescence, chemiluminescence, phosphorescence, light scattering, change in absorbance spectrum, change in emission spectrum, etc. The optical fiber allows for the optical monitoring of the progress/occurrence of an event at different sites on the surface of the fiber using light fed into the core of the fiber. Light leaking out of the fiber core is used to detect the progress or occurrence of an event. For example, the light may excite a chromophore at the site of the event. The time delay between the excitation pulse and the return signal can then be used to calculate the location of the detected event along the fiber. The location of the detected event can then be used in identifying the chemical compound at that site. Since the agents are distributed along the length of the optical fiber, rather than at the end of a set of fibers, the entire linear array can be analyzed with as few as one optical alignment of the optical fiber.

Chemosensors may also be arranged linearly along an optical fiber support. A linear array of hundreds to thousands of chemosensors may be placed along an optical fiber. These chemosensors are designed to assay for the presence or activity of particular chemical compounds or functional groups. If the chemosensor detects the presence of the chemical compound or functional group, a change in an optical property associated with the chemosensor, such as fluorescence, can be detected using the optical fiber as described above.

In another aspect, the present invention provides a novel method of synthesizing an array of compounds on an optical fiber. The compounds are synthesized off of functional groups on the optical fiber or on the cladding of the optical fiber. The functional groups are subjected to a series of reactions conditions, wherein each set of reaction conditions cycles with a specific period along the support. Each reaction condition of the series is identifiable as a function of distance along the fiber. This parallel method of synthesis along a linear optical fiber support allows each newly synthesized compound to be identified by its position along the fiber.

In yet another aspect, the present invention provides a method of analyzing the agents along the array. The compounds in the array can be assayed based on any desired activity. The assay will change an optical property at the site of the compound based on whether the compound has the activity being assayed for. Preferably, the optical characteristic measured is fluorescence. The compounds along the fiber can be distinguished in the time domain by excitation with a very narrow laser pulse, and detection of the resulting fluorescence emission that has been captured by the fiber. An enormous advantage of such a linear array along an optical fiber is that alignment of only one end of the fiber is needed to couple excitation and emission to every sensor element. The present invention also provides a system for analyzing the agents along the linear array. The system comprises a light source, a linear array of agents on a optical fiber, and a detector.

BRIEF DESCRIPTION OF THE DRAWING

FIG. 16 shows a system similar to the one shown in FIG. 15 but with a modified detection scheme. The fluorescence is dispersed according to wavelength by a grating (blazed, if required).

DEFINITIONS

Figure 1:
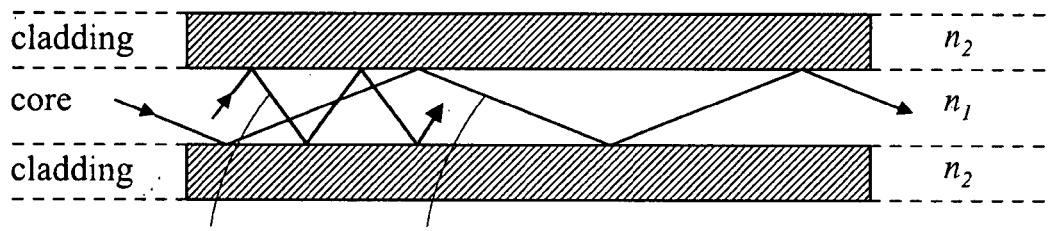
FIG. 1 shows a cross-section of an optical fiber along the direction of propagation of light.

Agent refers to any material which may be arranged linearly along an optical fiber. The term agent includes, but is not limited to, polynucleotides, peptides, proteins, organic molecules, chemical compounds, magnetic materials, and nanomaterials. In a preferred embodiment, the agents are small molecules. In a particularly preferred embodiment, the agents are members of a combinatorial library which has been synthesized along the optical fiber.

Chemosensor refers to a material which can detect the presence of a particular chemical compound (e.g., tryptophan, cholesterol, glucose, urea, cocaine, ethanol) or class of compounds (e.g., protein, sugars, metals, lipids, amines, aromatic compounds, opiates, alcohols, polynucleotides). The chemosensor may be a chemical compound, protein, peptide, receptor, catalyst, polynucleotide, etc. Preferably, in the presence of the compound detected by the chemosensor, the chemosensor undergoes a change in an optical property.

Chromophore refers to a chemical compound which absorbs or refracts light. In a preferred embodiment, the chromophore is a fluorophore and releases a photon of light upon being excited by a photon of a certain wavelength. In another preferred embodiment, the chromophore releases light by phosphorescence. In yet another preferred embodiment, the chromophore releases light by chemiluminescence.

Event refers to any reaction or interaction; preferably, the event results in a change in an optical property at the site of the event. In a preferred embodiment, the event is binding of an antibody, receptor, or other molecule to an agent on the optical fiber. In another preferred embodiment, the event may result in a change in the chemical structure of the agent on the optical fiber. In yet another embodiment, the event is a reaction in a series of steps to create a combinatorial library.

Optical fiber refers to a filament of transparent dielectric material, usually glass or plastic, that guides light. The optical fiber may or may not have a cladding around a core of similar geometry. Preferably, the light is coupled into the core of the fiber, being reflected from the core-cladding boundary and reflected into the cladding. Preferably, the refractive index of the core is higher than that of the cladding for the light to be guided by the fiber. In a preferred embodiment, light is transmitted through the fiber loss-free.

Peptide or protein, according to the present invention, means a chemical compound in which a string of at least three amino acids are linked together by peptide bonds. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc.

Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyladenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxyadenosine, 8-oxoguanosine, O(6)-methylguanine, and 2-thiocytidine), chemically modified bases, biologically modified bases (e.g., methylated bases), intercalated bases, modified sugars (e.g., 2'-hydroxylribose, 2'-fluororibose, ribose, 2'-deoxyribose, and hexose), or modified phosphate groups (e.g., phosphorothioates and 5'-N-phosphoramidite linkages).

Reactant region refers to a segment of the optical fiber which has agents attached to it. In the case of a combinatorial library, the reactant region is exposed to a specific set and sequence of chemical reaction conditions to create a member of the library. In the case of chemosensors along the optical fiber, the reactant region contains at least one type of chemosensor. Preferably, each region contains one type of chemosensor.

DETAILED DESCRIPTION OF PREFERRED EMBODIMENTS

An optical fiber provides a unique substrate on which chemosensors, combinatorial libraries, or other agents can be linearly arrayed and can be assayed based on a change in an optical property. The individual agents can be identified by their location along the fiber, and the time delay between delivering light and detecting a change in light can be used to determine the location and therefore the identity of the compound. Any optical property may be measured, including phosphorescence, chemiluminescence, fluorescence, light scattering, change in absorbance spectrum, change in emission spectrum, etc. The assaying of agents along an optical fiber using light allows for fast, complete analysis of the entire array.

Optical Fiber

The optical fiber provides a support for attaching a number of linearly arranged agents and a means for assaying these agents using light. FIG. 1 shows a cross-section through an optical fiber along the direction of propagation of light. The fiber consists of a core region with a refractive index $n_1$ and an optional cladding surrounding the core with refractive index $n_2$. The fiber may also include a jacket surrounding the cladding for mechanical protection of the core and cladding. The light transmitted by the fiber is coupled into the core of the fiber, being reflected from the core-cladding boundary and refracted into the cladding. If $n_2 < n_1$, then total internal reflection conditions exist for incident angle $\alpha$ with $\alpha \geq \alpha_g$ (the total internal reflection angle), where $\alpha_g = \arcsin(n_2/n_1)$. Under these conditions, light is confined to the core and is propagated loss-free. Even under total internal reflection conditions, the electromagnetic light wave in the core will show exponential intensity decay into the "forbidden" cladding region (the evanescent wave). A chromophore located close to the core/cladding boundary can then absorb the light becoming electronically excited. According to geometrical ray optics light emitted from the chromophore cannot be coupled back into the core such that loss free propagation in the core regions will occur. However, the evanescent tails of the guided light modes in the core can pick up the emitted light intensity from the cladding region and transmit this intensity loss-free through the core region.

Figure 2:
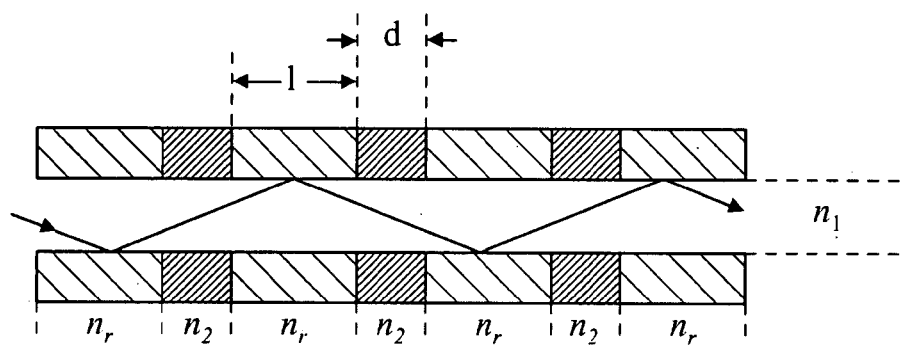
FIG. 2 shows the distribution of reactant regions on an optical fiber. The lightly shaded regions of length l contain reactants; these regions are separated by a distance d. The index of the original cladding is $n_2$, while $n_r$ is the refractive index of the substituted cladding that acts as the host for the reactants.

In a particularly preferred embodiment of the invention, equidistant reactant regions of equal length are created along the length of an optical fiber (FIG. 2). More preferably, the optical fiber comprises a core surrounded by a cladding, and the reactant regions span the entire circumference of the cladding. Each reactant region has the length l and is separated from adjacent reactant regions by the distance d. The choice of l and d depends on which sample property will be monitored and which detection method will be chosen.

In the case of an optical fiber comprising a core surrounded by at least one layer of cladding, one possibility is to use the cladding of the optical fiber as the host for the reactants or for coupling the chemosensors. The advantage is that the basic layout of the optical fiber is undisturbed, meaning that the total internal refraction angle is constant along the fiber. However, from a chemical point of view, the existing cladding may limit the chemistry that can take place there. Also, since the cladding is typically a high-density material, the diffusion of reactants into the cladding is slow. Therefore, a better approach is to remove the cladding where reactant regions are to be created and replace it with another host material that preferably has one or more of the following characteristics: 1) allows for many chemical reactions to take place; 2) allows for reasonably rapid diffusion rates of the reactants; and 3) possesses a refractive index that is equal to the original cladding. If the index of refraction of the replacement cladding is greater than that of the original cladding, losses of light intensity will result as discussed below in case 2. Replacement claddings include sol-gel matrices, resins, plastics, polymers, polysaccharides (e.g., agarose), etc.

Depending on the relative magnitudes of the refractive indices of core $n_1$, cladding $n_2$, and cladding replacement $n_r$, several cases can be distinguished as discussed below:

Case 1: $n_1 > n_2 = n_r$

In this case, the fiber behaves optically like an unmodified fiber and the total internal reflection angle $\alpha_g$ is unchanged along the length of the fiber. Excitation of fluorophores in the cladding can only occur through evanescent waves. Since the intensity of evanescent waves drops off exponentially away from the boundary, only fluorophores close to the core-cladding boundary will be excited. The light emitted by these fluorophores can enter the fiber core by refraction and through evanescent pickup. Only light transferred to the core through evanescent coupling can propagate through the fiber core as guided waves. The advantage of this scheme is that the attenuation of the core light intensity is small. On the other hand, this implies that only a small number of photons are available to excite the fluorophores. Also, as mentioned above, from the subsequently emitted light, only the fraction that is coupled back into the core through evanescent pickup is available as signal. A slight improvement in core collection efficiency could be achieved by bending the fiber at the reactant regions, provided that the reactions take place on only one side of the fiber.

Case 2: $n_1 > n_r > n_2$

Figure 3:
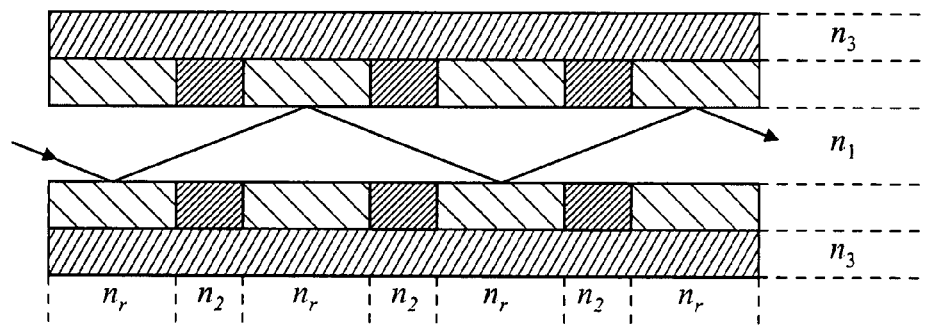
FIG. 3 shows an optical fiber with an additional layer of cladding with refractive index $n_3$.

This is essentially identical to case 1, except that the total internal reflection angle from core to the cladding with refractive index $n_r$ is now given by $\alpha'_g = \arcsin(n_r/n_2) \sin \alpha_g$. For $n_r > n_2$, coupling into the cladding is increased since incident angles $\alpha$ with $\alpha_g > \alpha > \alpha'_g$, which are coupled into the fiber under guided condition, are now refracted into the cladding. This leads to larger fluorescence intensities due to larger excitation and due to the fact that fluorophores farther away from the core-cladding boundary may be excited. However, the overall core light intensities are reduced. Also, fluorescence photons emitted with angles $\beta < \arcsin(n_2/n_r)$, with respect to the surface normal, will propagate in the core as guided modes. It depends on the emission characteristics of the fluorophores, whether this scenario is favorable or not. If after a reaction, no fluorophores are in a reactant region, the light is lost to the cladding (i.e., no fluorescence return signal), unless it can be retrieved by coupling it back into the fiber. A fiber configuration that could meet these requirements is shown in FIG. 3.

An additional layer of cladding with refractive index $n_3$ may be added to the fiber. Light that enters the reactant regions then encounters an additional boundary for reflection and refraction. Light that enters the reactant region and that is not absorbed by a fluorophore is reflected back into the core as a guide mode if $n_3 = n_2$, which can be easily verified. One problem that remains with this approach is that the reactant regions are shielded from reactants by the additional cladding layer. In this case, but not in other cases, the roughness of the surface of the sensor region and its thickness are of importance. Another feature of this case is that capture of the emission from the sensor region does not decay exponentially with distance from the reactant region/core interface.

Case 3: $n_1 > n_2 > n_r$

This case is similar to case 2, except that the magnitudes of the refractive indices $n_2$ and $n_r$ are interchanged. This case is more likely to occur in practice, as the refractive indices of suitable replacement cladding serving as hosts to reactants are likely to fall into this category. Coupling will be only be evanescent wave.

Case 4: $n_1 < n_r$ and $n_r > n_2$

In this case, coupling from core to reactant region is for the present incident angles via refraction, meaning strong loss of core light intensity. The emitted fluorescent light with incident angles $\beta$ for the cladding-core transition between $\arcsin(n_2/n_r) < \beta < \arcsin(n_1/n_r)$ will propagate in the core as guided modes. An additional layers of cladding as discussed in case 2 could serve to reflect light emitted onto the $n_r$-$n_3$-interface (FIG. 3) back into the fiber, enhancing the signal intensity in the core.

Figure 4:
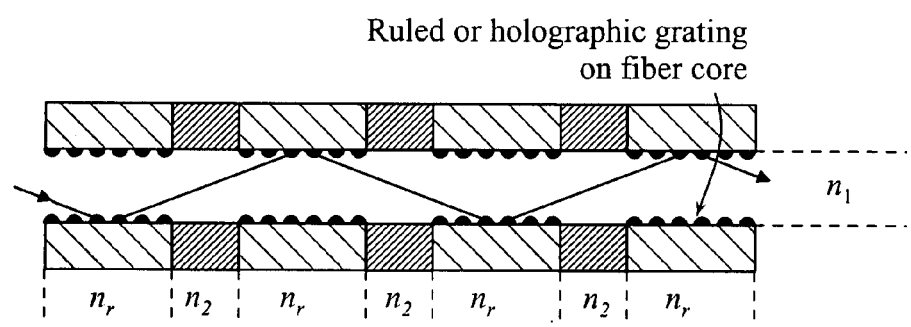
FIG. 4 shows enhancement of the core-cladding and cladding-core coupling efficiency using a grating at the fiber-cladding interface.

In another preferred embodiment, a grating (either ruled or holographic) at the interface between the core and reactant regions of the optical fiber is used to increase the core-cladding and cladding-core coupling efficiency (FIG. 4). For the transition from core to substituent cladding (with $n_r$), light incident onto the core surface under the total internal reflection angle $\alpha_g$ is diffracted into the cladding according to $$\beta_g = \arcsin n_2/n_{r-m/d\lambda_{vac}}$$

where $\beta_g$ is the diffraction angle for $\alpha = \alpha_g$, d is the spacing of adjacent grating lines, and $\lambda_{vac}$ is the wavelength of light in vacuo. For the internal reflection angle, $\alpha'_g$ this expression is $$\beta'_g = \arcsin 1 - m/d\lambda_{vac}.$$

Using $1/d = 600$ mm$^{-1}$; $n_r = 1.45$; $n_1 = 1.5$; $\lambda_{vac} = 338$ nm, one obtains $\beta'_g = 52.8°$ for m=1 and $\beta'_g = 36.4°$ for m=2. Without the grating, no light could enter the cladding under these conditions. This demonstrates that a grating can significantly enhance the coupling efficiency. Using the grating equation for the transition of the emitted light back to the core, the range of incident angles $\beta''$ (with respect to the surface normal) of emitted light such that propagation in the core occurs as guided modes is given by $$\beta'' > \beta''_g = \arcsin n_2/n_r - (n_1/n_r)(m/d)\lambda_{vac}.$$

Using $1/d = 600$ mm$^{-1}$; $n_2 = 1.5$; $n_r = 1.45$; $n_1 = 1.5$; $\lambda_{vac} = 550$ nm, the following incident angle ranges lead to guided core modes: $\beta'' > 74.9°$ (refraction only), $\beta'' > 38.6°$ (diffraction, first order m=1), and $\beta'' > 16.4°$ (diffraction, second order m=2). Clearly, grating coupling significantly enhances the collection of the fluorescence into guided core modes.

In another preferred embodiment, more than one optical fiber is used. These fibers may contact one another along one side, be intertwined, or be braided together. One fiber may be used to excite the fluorophore and the other used to detect the fluorescence emitted. Either the excitation or detection fiber may have the agents on its surface. In a particularly preferred embodiment, the optical fibers only contact each other at reactant regions. These embodiments of the present invention that use more than one optical fiber are discussed in more detail below.

Attachment of Agents to Optical Fiber

Agents may be attached to the optical fiber using any means available. The agents may be associated with the optical fiber through direct or indirect covalent or non-covalent interactions although covalent attachment is preferred. In a particularly preferred embodiment, the surface of the optical fiber or, optionally, the optical fiber's cladding, if one is present, is derivatized to provide functional groups for attachment of the agents. Examples of derivatizations is aminopropylsilylation by silylation, silylation, adsorption of a chemical compound onto the surface of the fiber, etc. Silylation of silica surfaces are well known in the art (Arkles Chemtech 7:766-778, 1977; incorporated herein by reference) and will provide fiber regions that can be further functionalized. The agents may optionally be attached to the optical fiber through a linker allowing the agents to be assayed more easily away from the surface of the fiber. In a preferred embodiment involving combinatorial libraries, the synthesis of libraries of compounds by the procedure described by Schwabacher et al. (J. Am. Chem. Soc. 121: 8669-8670, 1999; incorporated herein by reference) is carried out on an optical fiber, the surface of which has been derivatized to provide functional groups for attachment and further functionalization of a core chemical compound. One example of a surface derivatization suitable for combinatorial synthesis is aminopropylsilylation. Other techniques include chemical treatments of organic surfaces such as ozonolysis, plasma etching, or adsorption of functionalized polymers or small molecules. Deposition of gold, or another material, followed by self-assembly of a monolayer, for example of functionalized thiols, constitutes another approach.

Distinct from such methods that place active groups at the core/cladding interface, one can place functional groups distributed throughout a sensor cladding phase. Materials appropriate for such phases include all materials useful as supports for solid-phase synthesis. These include polystyrene, polysaccharides, polyacrylamides, polyethylene glycols, silica gels, and others.

Method of Preparing Library

The method used to synthesize a combinatorial library as a linear array along an optical fiber is similar to the technique taught by Schwabacher et al. (J. Am. Chem. Soc. 121(37):8669-8670, 1999; incorporated herein by reference). In summary, an optical fiber is provided having reactive groups, and various reactant regions along the fiber are subjected to a set of reaction conditions so that the reaction conditions cycle with a specific period along the fiber. The set of reaction conditions that any one section of the fiber was subjected to is determinable from the position along the fiber. As one of ordinary skill in the art will realize, in order to generate more complex libraries of compounds, it is desirable to subject the fiber to more than one set of reaction conditions, and it is also desirable to provide the maximum number of combinations possible for a given set of reaction conditions. Thus, the support is ideally subjected to two or more sets of reactions conditions. In a preferred embodiment, each subsequent set of reaction conditions is cycled with a specific period along the support with respect to other sets. In certain preferred embodiments, the periods are obtained by winding a support or thread around a geometric template and then dividing the surface of the geometric template into regions across the direction of the thread. In another preferred embodiment, a library may have duplicate compounds by utilizing a solid support longer than necessary to produce a single copy of each library member.

Method of Analyzing Array

Figure 5:
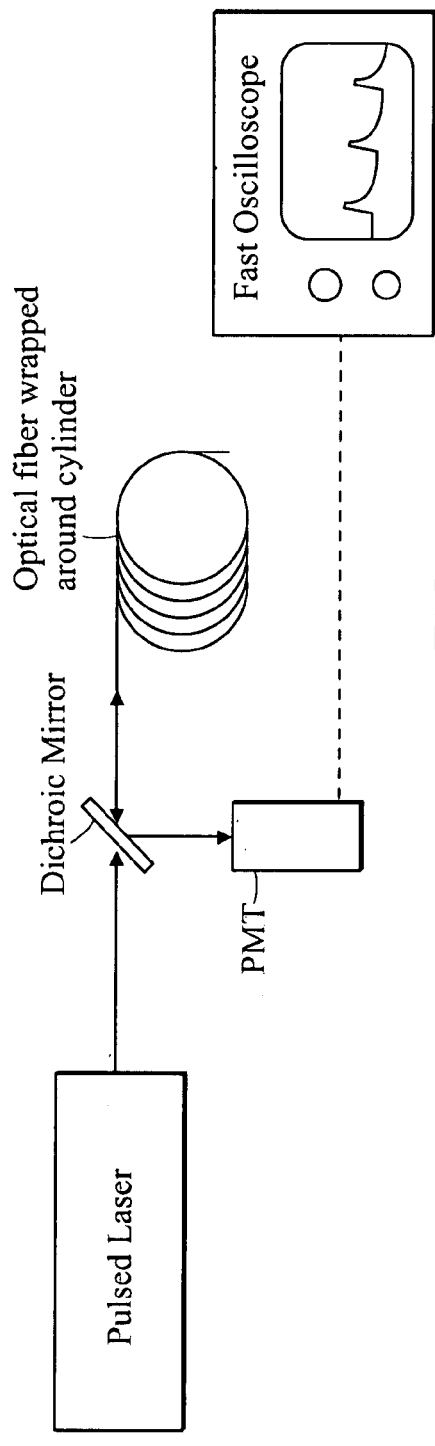
FIG. 5 shows a basic setup for analyzing a linear array of agents on an optical fiber. A photomultiplier tube (PMT) connected to a fast oscilloscope records the fluorescent light emitted into the fiber after pulsed laser excitation through the fiber.

As will be appreciated by one of ordinary skill in this art, analysis of an array of agents on an optical fiber can be done using any assay involving a change in an optical property. Examples of optical properties useful in the present invention include fluorescence, phosphorescence, chemiluminescence, light scattering, change in absorbance spectrum, change in emission spectrum, etc. To give but one example, a combinatorial library may be assayed for the ability of the members of the library to bind a specific protein. The protein may be labeled with a fluorophore, and the library on an optical fiber may be contacted with a solution of the labeled protein. The basic experimental setup shown in FIG. 5 could then be used to assess the binding of all members of the library to the protein. The advantage of this system is that all members of the library could be, quickly with one optical alignment of the optical fiber, analyzed for their ability to bind the protein.

The system used to analyze the library comprises a light source (e.g., laser, diode laser, gas laser, dye laser, solid state laser, plasma tube laser, LED), the optical fiber, and a detector (e.g., photomultiplier tube (PMT), charge-coupled devices (CCD), avalanche photodiode, multi-channel plate, photodiode arrays). Light pulses are fed into the optical fiber. In the case of fluorescence, fluorophores (if they are present after a reaction or assay of the library) in the reaction regions along the fiber are excited, and the light emitted by the excited fluorophores propagates back through the fiber. These signals from the fluorophore are detected and analyzed in the time domain since signals from fluorophores located at different locations along the fiber arrive at different times. Therefore, the spatial location of the fluorophore is encoded in the time domain. The quantities which can be measured by this system using a fluorophore are changes in fluorescence intensity, lifetime, and wavelength.

The lengths d and l (as described above) on the optical fiber depend on which of these quantities will be measured and the time-constant of the experiment. Assuming that a light pulse enters the fiber at time t=0 and position along fiber x=0, for a fluorophore located at the "front" end of a reaction region at position $x=x_1$, the return pulse exites the fiber at x=0 at time $$t_1 = 2xn_1/c_{vac},$$

where $c_{vac}$ is the speed of light in vacuo and $n_1$ is the refractive index of the fiber core. The time difference between the arrival of this return signal and the return signal from a fluorophore located at the "front" end of the following reactant region at position $x=x_2=x_1+l+d$ (see FIG. 2) is $$\Delta t = t_2 - t_1 = 2(l+d)n_1/c_{vac}.$$

All fluorophores within one reactant section should contribute to one return signal characteristic a for this particular section. In order to minimize overlaps of the fluorescence traces from fluorophores in one reactant section due to sequential excitation, the length l of the reactant section has to be less than the spatial width $\Delta s_p$ of the exiting laser pulse.

$$l << \Delta s_p = c_{vac}\Delta t/n_1,$$

where $\Delta t_p$ is the temporal laser pulse length. For example, where $\Delta t_p=0.5$ ns and $n_1=1.5$, l<<10 cm. If this condition is satisfied, the spatial extent of the reactant region can be neglected to a good approximation for the interpretation of the return signal. Using the assumption $l \approx 0$, $$\Delta t = t_2 - t_1 = 2dn_1/c_{vac}.$$

The minimum separation of reactant regions $d_{min}$ is determined by the bandwidth of the oscilloscope and/or the response time of the photomultiplier tube. For example, for a 1 GHz oscilloscope, $d_{min}=10$ cm for $n_1=1.5$.

If the goal is the detection of changes in fluorescence lifetime of the fluorophore upon reaction, the spacing between successive reactant regions must be increased. This can be shown as follows. Assuming a single-exponential fluorescence decay with time constant $\tau$, in order to extract $\tau$ from the measured decay curve, a signal trace of approximately $5\tau$ is required depending to some extent on the signal/noise ratio. To avoid overlap of the fluorescence traces from successive reactant regions, the separation of successive reactant regions has to be $$d_{5\tau} = 5(\tau c_{vac}/2n_1).$$

Assuming a fluorescence lifetime of $\tau=5$ ns yields $d_{5\tau}=250$ cm. Often fluorescence lifetimes are less than 5 ns, particularly for fluorophores in solid host matrices. Also, signal averaging can greatly improve the signal/noise ratio, reducing the time interval needed for a reliable extraction of $\tau$. Therefore, $d_{5\tau}=250$ cm is preferable for the separation of the reactant regions. However, even for this scenario the one-dimensional combinatorial chemistry technique on optical fibers can still be employed, and alternatively, optical delay lines for excitation and detection may be used as described in detail below.

In another preferred embodiment, a different approach involving either detecting the fluorescence signal outside of the optical fiber or exciting the fluorophore using a light source outside the optical fiber is used in analyzing the library. The latter approach reduces some of the problems associated with delivering photons into the reactant regions and then delivering the emission photons from the excited fluorophore back into the core. The excitation of the reactant regions may be through the optical fiber, and the detection of the fluorescence signal radiating off the side of the fiber (i.e., detection does not take place through the fiber); or in another preferred embodiment, excitation of the reactant regions is accomplished by illuminating the side of the fiber and detection of fluorescence signal is through the fiber.

Figure 6:
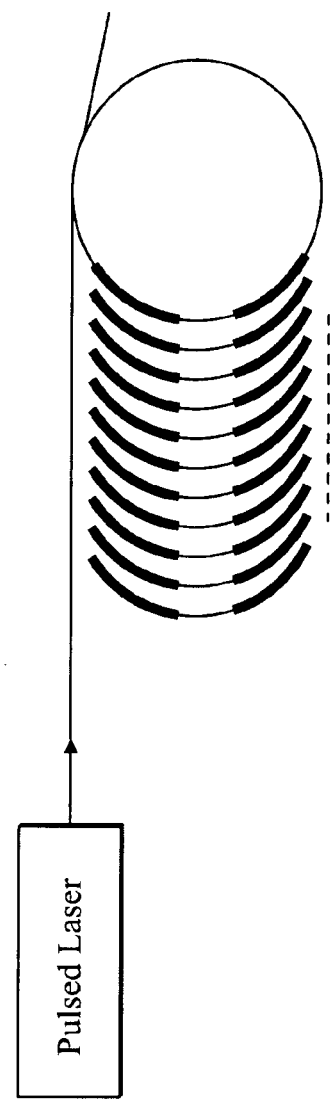
FIG. 6 shows a system for analyzing an optical fiber mounted on a cylinder. The dark lines represent the reactant regions.
Figure 7:
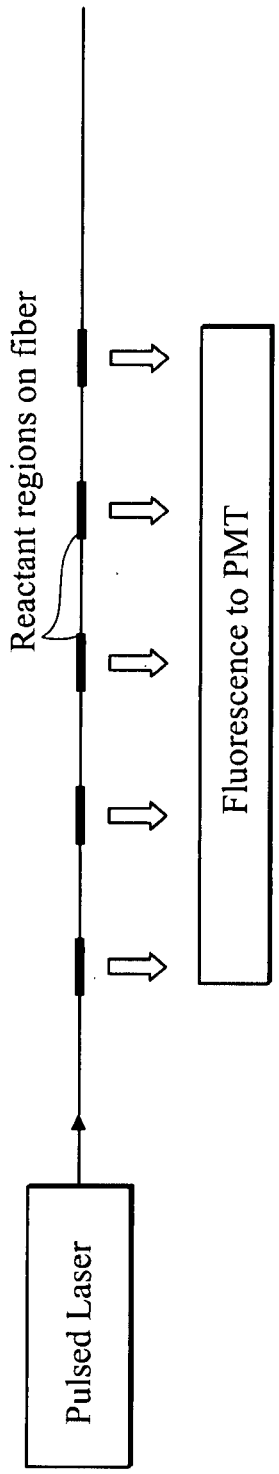
FIG. 7 shows "sideways" detection of the fluorescence emitted by the reactant regions for a linear fiber.
Figure 8:
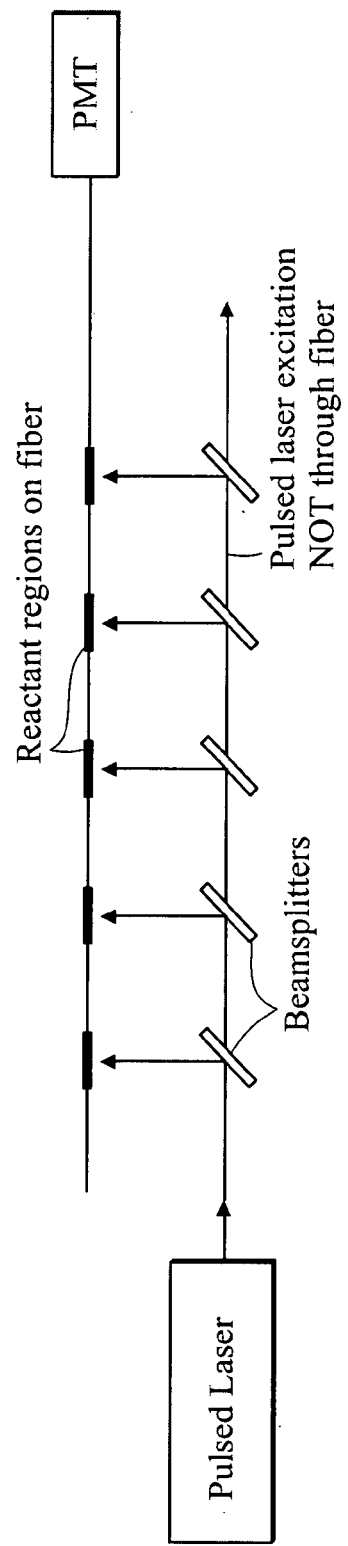
FIG. 8 shows "sideways" excitation of the reactant regions on the fiber. The fluorescence is picked up by the fiber and guided to the PMT.

FIGS. 6-8 show various approaches to using this method. The optical fiber can be mounted on a cylinder as shown in FIG. 6. Light emitted from the reactant regions after excitation through the fiber can also be detected by placing a detector close to the side of the fiber as shown in FIG. 7. The time separation of the fluorescence signals of successive reactant regions is determined by their spatial separation. Compared to the basic detection scheme shown in FIG. 5 and described above, the separation is reduced by a factor of 2. The excitation and detection may also be reversed as shown in FIG. 8. The reactant region(s) can then be excited by a light source (e.g., a laser), and the light emitted from the excited fluorophore can be detected through the fiber.

Figure 9:
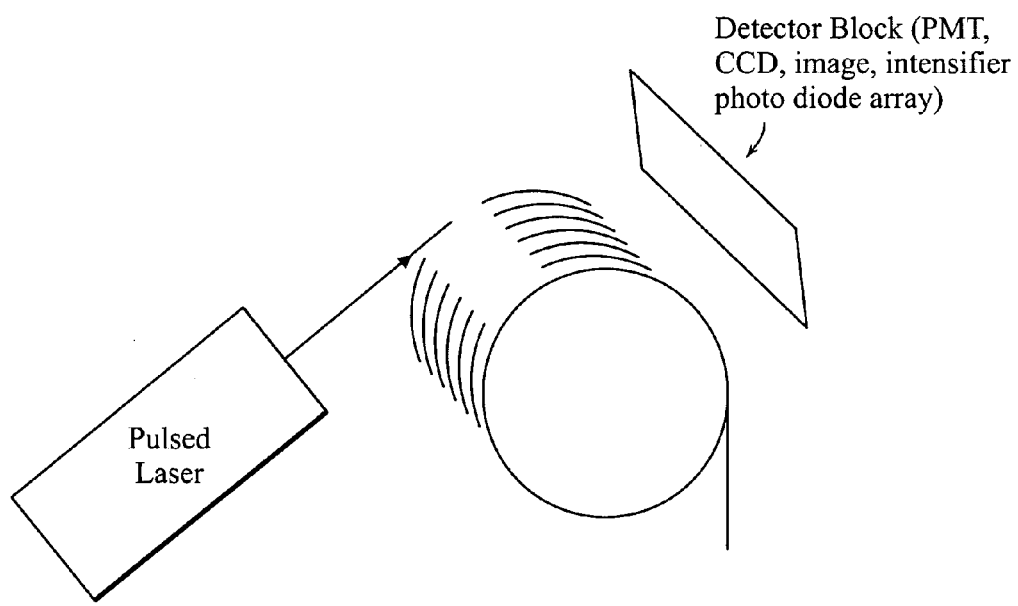
FIG. 9 shows a scheme for detecting the fluorescence emission off the side of reactant regions for the case of a fiber on a cylinder. A detector block facing the sides of the reactant regions on the fiber was added. Possible detectors include photomultiplier tube(s), charge coupled devices (CCDs) with or without image intensifiers, and photodiode arrays.

The time separation of the signal is mainly determined by the spatial separation of the reactant regions on the fiber. In FIGS. 7 and 8, the fiber is shown in a straight line; however, this configuration is not necessary. Preferably, since the fiber is mounted on a cylinder when the reactions are carried out, the presence of the fluorophore is detected while the fiber is still mounted. FIG. 9 shows a scheme for detecting the emission off the side of the reactant regions for the case of a fiber mounted on a cylinder. A detector block facing the sides of the reactant regions on the fiber was added to the scheme shown in FIG. 6. Possible detectors include photomultipliers tube(s) (PMT), charge coupled devices (CCD) with or without image intensifiers, and photodiode arrays.

Figure 10:
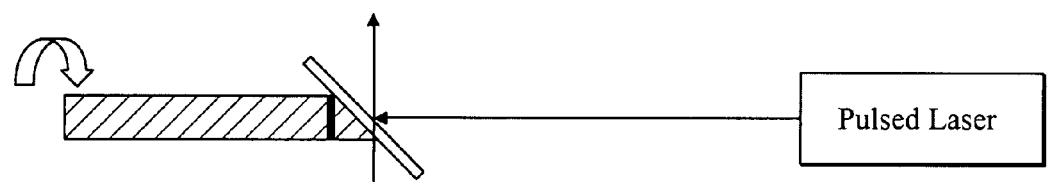
FIG. 10 shows a mirror mounted at 45 degree on a rotating rod, causing the laser light directed onto the mirror to rotate in space.
Figure 11:
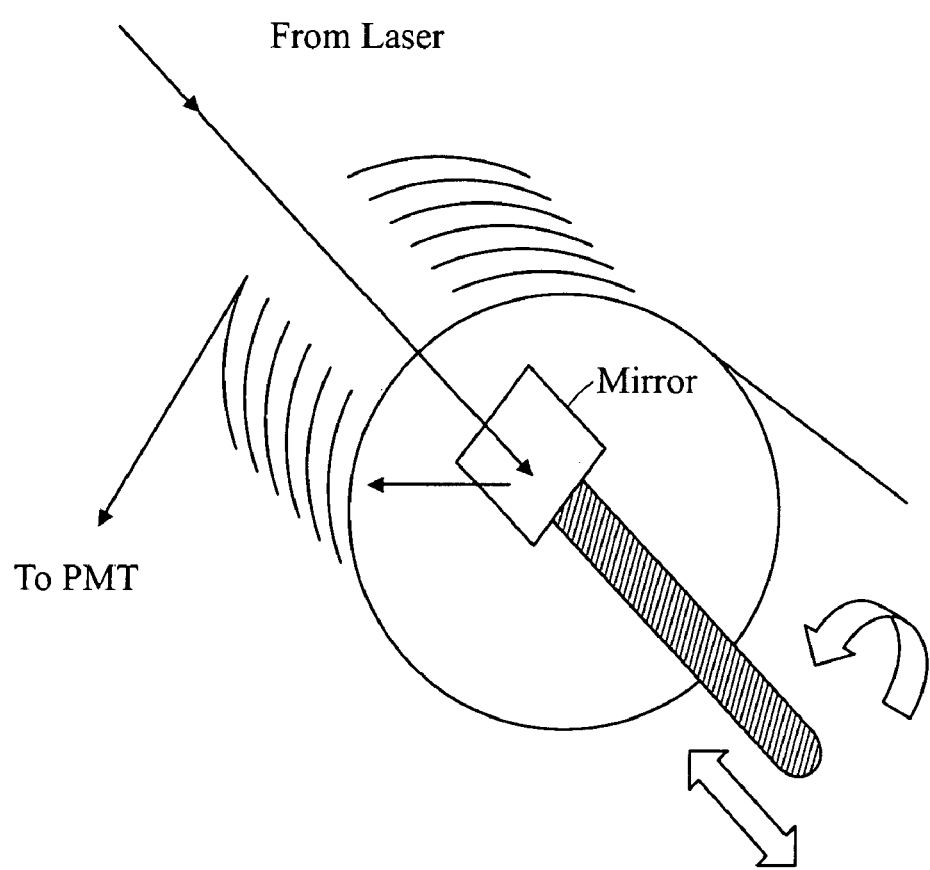
FIG. 11 shows a rotating mirror mounted inside of the cylinder. The laser beam is widened with cylindrical lenses to excite a range of reactant regions.

In another preferred embodiment, the fiber is mounted on a hollow, transparent cylinder. A rod is inserted into the cylinder parallel to the cylinder's axis. One end of this rod is cut at an angle, and a mirror is mounted onto the end (FIG. 10). The rod and mirror can then rotate, and a laser beam that is directed on the mirror can trace the inside of the cylinder and excite the reactant regions (FIG. 11). The photons from the excited fluorophores can then be detected through the optical fiber or off the side of the reactant regions.

The laser beam is widened with cylindrical lenses to excite a range of reactant regions along the cylinder's axis. This can also be controlled by mounting the rod on a translator stage. The mirror rotation frequency has to be commensurate with the pulse repetition rate of the laser. The scheme will also allow for reduced separation of the reactant regions, since only reactant regions separated by a full circumference of the cylinder will be excited simultaneously. Successive reactant regions on the fiber will be excited as the mirror rotates. An equivalent scheme without moving parts would entail excitation diode lasers or diode LEDs mounted around the coiled fiber. Other schemes to address the separation of reactant regions are addressed in the following section.

As described above, to determine changes in fluorescence lifetimes, the decay of fluorescence intensity has to be monitored for a certain time interval. To avoid overlap of the fluorescence decays of two successive reactant regions, these regions have to be separated roughly by a distance $d_{5\tau}$. For long fluorescence lifetimes, the necessary separations can become quite large, which means that the overall length of the fiber for large compound libraries can be substantial. Assuming a fluorescence lifetime of $\tau=5$ ns and a total of 1000 reactant sites, the total fiber length would need to be 2.5 km. Several schemes that allow for a closer packing of the reactant regions under these circumstance have been envisioned.

Figure 12:
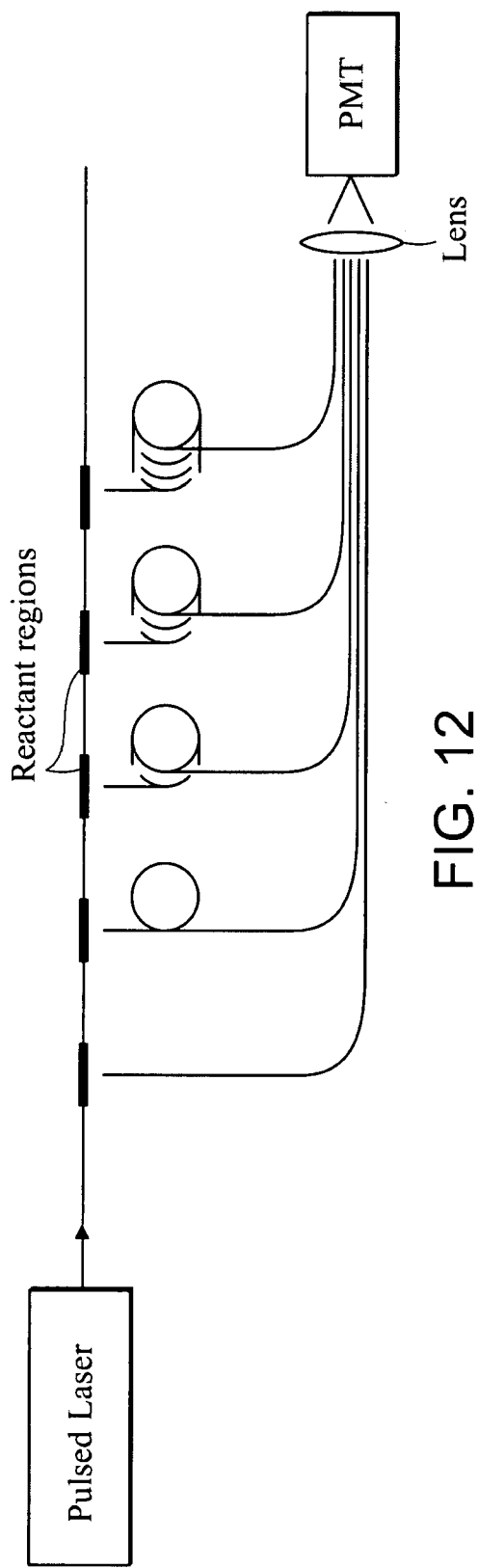
FIG. 12 shows the N+1 fiber scheme: one excitation fiber, which also supports the reactant regions with a detection fiber for each of the N reactant regions. The pickup fibers have different lengths to delay the arrival of the fluorescence signals from different reactant regions at the detector (PMT).

Use of more than one optical fiber. In a preferred embodiment, the reactant regions can be spaced almost arbitrarily close if different fibers for excitation and detection are employed. As shown in FIG. 12, the fiber supporting the reactant regions is used for the excitation of the fluorophores; however, instead of monitoring the fluorescence through this fiber, the fluorescence of each reactant region is picked up by a separate fiber and guided to a detector (e.g., photomultiplier tube). Since coupling into the fiber end is very efficient, the signal intensity is expected to be quite reasonable. By varying the relative lengths of the pickup fibers, the delay between the arrival of fluorescence signals at the detector can be adjusted as desired by lengthening the fibers carrying the signal from the fluorophores as indicated in FIG. 12. An advantage of this scheme is that chemical reactions on the excitation fiber can be carried out separate from the detection assembly. The detection fibers can be mounted in a metal block. For readout, the excitation fiber is placed on the metal block such that reaction regions and pickup fiber entrance surfaces match. An additional advantage is that the fluorescence signal does not have to pass other reactant regions on the way to the detector. This avoids potential sources for signal attenuation. However, for a large number N of reactant regions, this detection scheme could be quite complex and costly. However, it could be multiplexed quite easily. The fiber bearing the reactant regions could be coiled as shown in FIG. 6, so that each pickup fiber receives light not from one but from many sensor regions. This allows distinction of the fluorescence return signals of the multiple sensor regions by time, their separation determined by the circumference of the coil.

Figure 13:
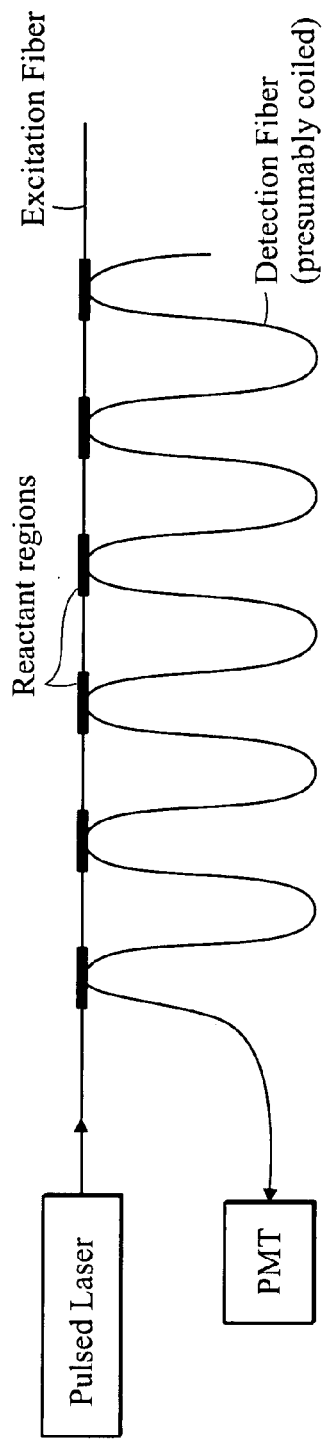
FIG. 13 shows the two fiber scheme: one excitation fiber containing the reactant regions and one detection fiber that periodically contacts the reactant regions.

A simpler detection scheme can be realized with only two fibers (FIG. 13). An excitation fiber supporting the reactant regions is periodically brought into contact with a detection fiber at the reactant regions as described in more detail below in the Examples. The light emitted by the fluorophores is coupled into the detection fiber. This coupling occurs through evanescent pickup. Again, as in the previous scheme shown in FIG. 12, the time delay between the arrival of two fluorescence signals at the detector can be adjusted by varying the length of the detection fiber between successive contacts with the reaction fiber. While being simpler, this scheme offers lower signal intensities.

Figure 14:
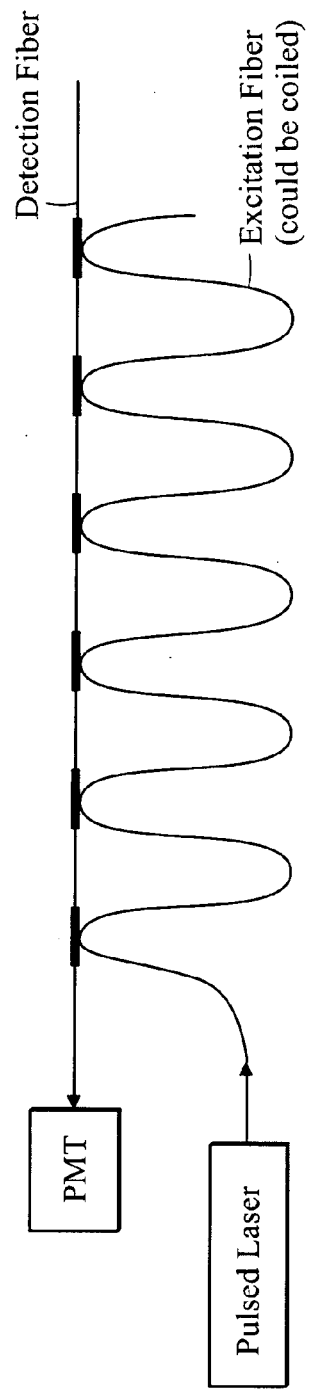
FIG. 14 shows another two fiber scheme: one detection fiber containing the reactant regions and one excitation fiber that periodically contacts the reactant regions.

Of course, a reverse of the scheme shown in FIG. 13 is also possible (FIG. 14). The fiber containing the reactant regions is now used as the detection fiber. The required time delay between successive signals at the detector is achieved by delaying the excitation light pulses.

Maximizing the information output from the signal. As mentioned above, the occurrence and results of reactions in the reactant regions on the fiber can be monitored analyzing changes in fluorescence intensity and fluorescence lifetimes. For a fiber containing thousands of reactant regions, the recorded signal stretches over a long time base (a spacing of $d5\tau=250$ cm for $\tau=5$ ns) producing a time trace $t_{tot}$ of approximately $t_{tot}=17$ µs. Averaging many time traces can significantly enhance the signal/noise ratio. The number of traces that can be recorded per second is determined by the pulse repetition rate R of the laser, provided that the time between two laser pulses 1/R is larger than $t_{tot}$. A further restraint is that one time trace of length $t_{tot}$ contains thousands of data points. High time resolution is required in order to be able to reliably extract fluorescence lifetimes from the return signals of individual reactant regions. Depending on the data storage capacity and averaging capability of the fast oscilloscope, after recording each trace or the averaged traces, the data points might have to be transferred to and stored on a computer. The time required for this operation determines the oscilloscope dead time during which no further data points can be recorded.

Figure 15:
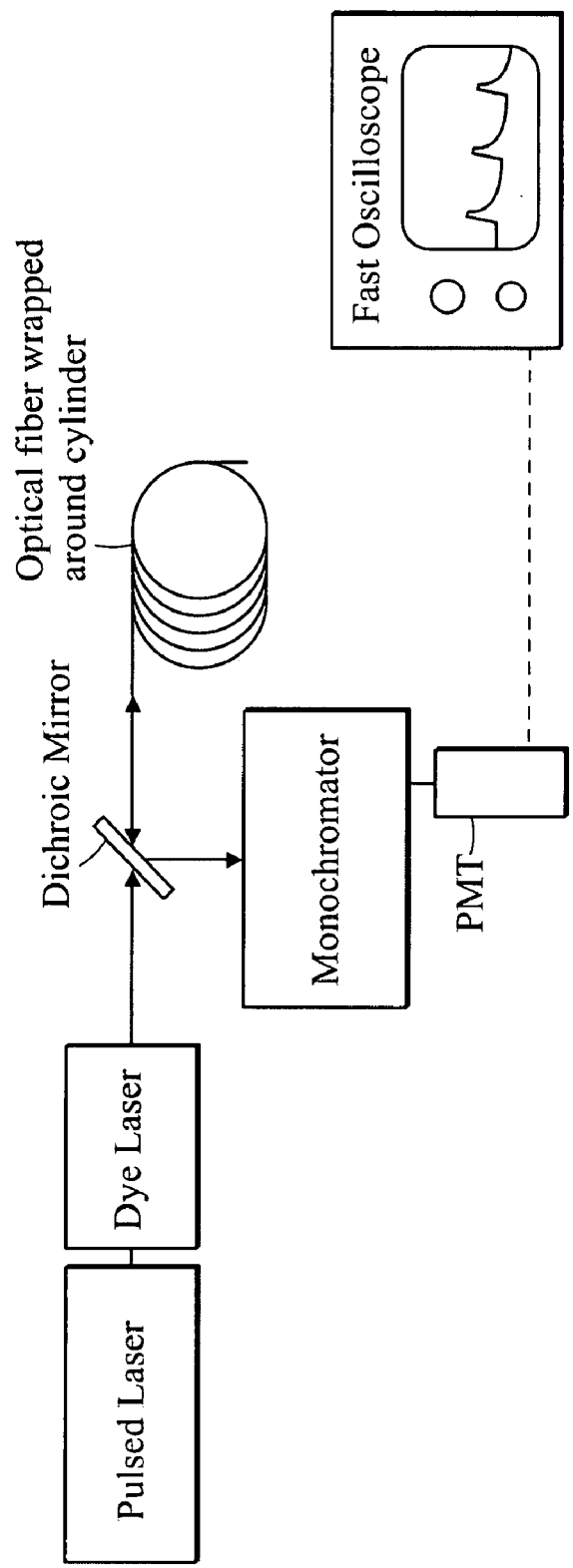
FIG. 15 shows a modified system for analyzing a linear array of agents on an optical fiber. A dye-laser provides variable excitation wavelengths, while a monochromator allows only fluorescence of a specified wavelength region to reach the detector (PMT). Depending on the desired spectral range to be recorded, the monochromator can be replaced with band-pass filters or cutoff filters.

Even more information can be extracted if the data is recorded under variations of the excitation wavelength. Moreover, instead of recording the integrated fluorescence over all wavelengths, only certain spectral regions of the fluorescence can be recorded by employing cutoff filters, band-pass filters, or monochromators (FIG. 15). Recording the fluorescence signal under variation of excitation and/or detection wavelengths would provide even more detailed information on the chemical reactions that took place in the individual reactant regions.

Figure 16A:
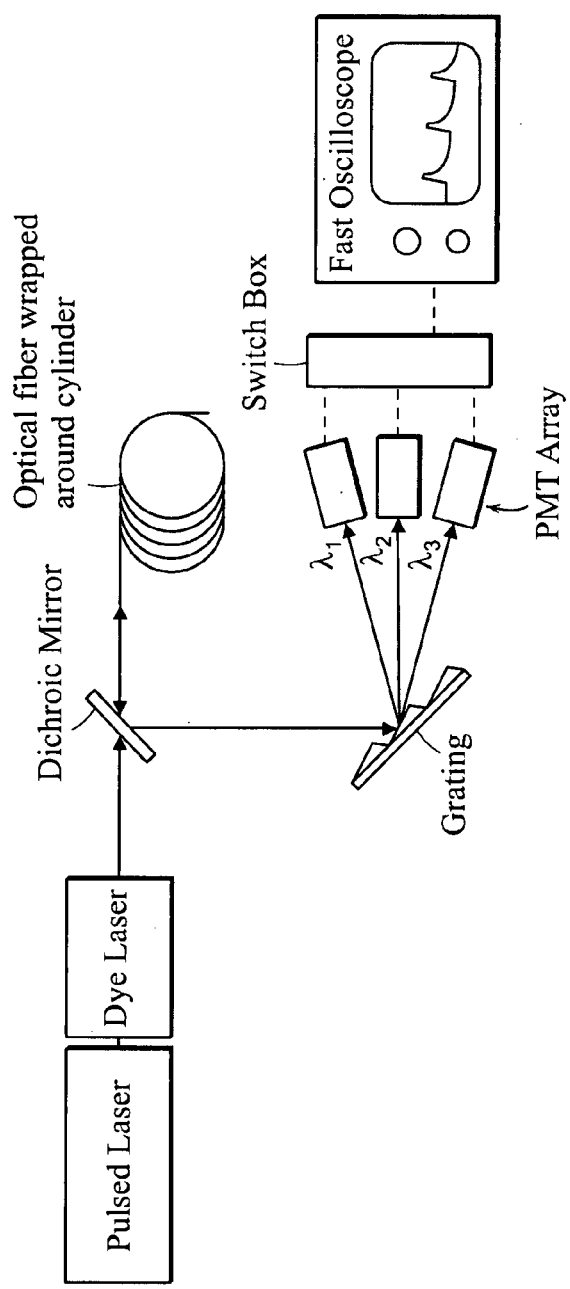
In FIG. 16a, the dispersed light is directed towards a set of photomultipliers (PMT), each detecting a certain wavelength region. A switch box allows selecting which PMT output is sent to the fast oscilloscope.
Figure 16B:
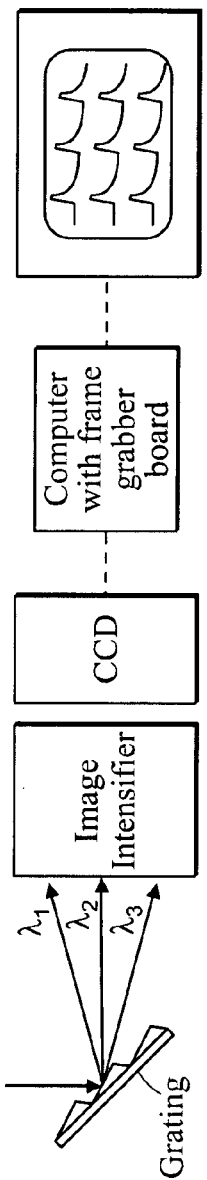
In FIG. 16b, the dispersed fluorescence is enhanced with an image intensifier and detected with a CCD array. A frame grabber ensures rapid removal of the data stored in the CCD to the attached computer. For high intensity signals, a photodiode array in place of a PMT array or a CCD is feasible.

The configuration shown in FIG. 15 relies on only one detector; however, in certain preferred embodiments, multiple detectors may be used (FIG. 16). In one particularly preferred embodiment, the fluorescence signal is dispersed according to wavelength by a grating (FIG. 16a). The dispersed light is directed towards a set of photomultiplier tubes each detecting a certain wavelength region. A switch box allows selecting which PMT output is sent to the fast oscilloscope. Alternatively, multiple oscilloscopes may be used. In FIG. 16b, the dispersed fluorescence is enhanced with an image intensifier and detected with a CCD array. A frame grabber ensures rapid removal of the data stored in the CCD to the attached computer. For high intensity signals, a photodiode array in place of a PMT array or a CCD is feasible.

For fibers containing thousands or more reactant regions the Fourier analysis scheme developed by Schwabacher et al. (J. Am. Chem. Soc. 121(37):8669-8670, 1999; incorporated herein by reference) is employed to elucidate the importance of each reaction step in synthesizing the final product. The analysis depends on the presence of repeat patterns of reactant regions on the fiber. Obtaining these repeat patterns is straightforward in the one-dimensional combinatorial chemistry scheme if the number of reaction steps S is significantly less than the number of reactant regions N, S<<N. Schemes developed for Fourier transform infrared spectrometers to cope with a limited range of data are, in principle, applicable to the schemes described here. Remedies, for example, include the use of apodization functions.

If the fluorescence decay time of a set of sensor regions is known to be constant or approximately so, this information can be used to obtain data rapidly with enhance dynamic range. By fitting the tail of a fluorescent decay that saturates the detector at its peak, information on signals much beyond the digitization scale may be obtained.

These and other aspects of the present invention will be further appreciated upon consideration of the following Examples, which are intended to illustrate certain particular embodiments of the invention but are not intended to limit its scope, as defined by the claims.

EXAMPLES

Example 1—Two Fiber Scheme

Figure 17:
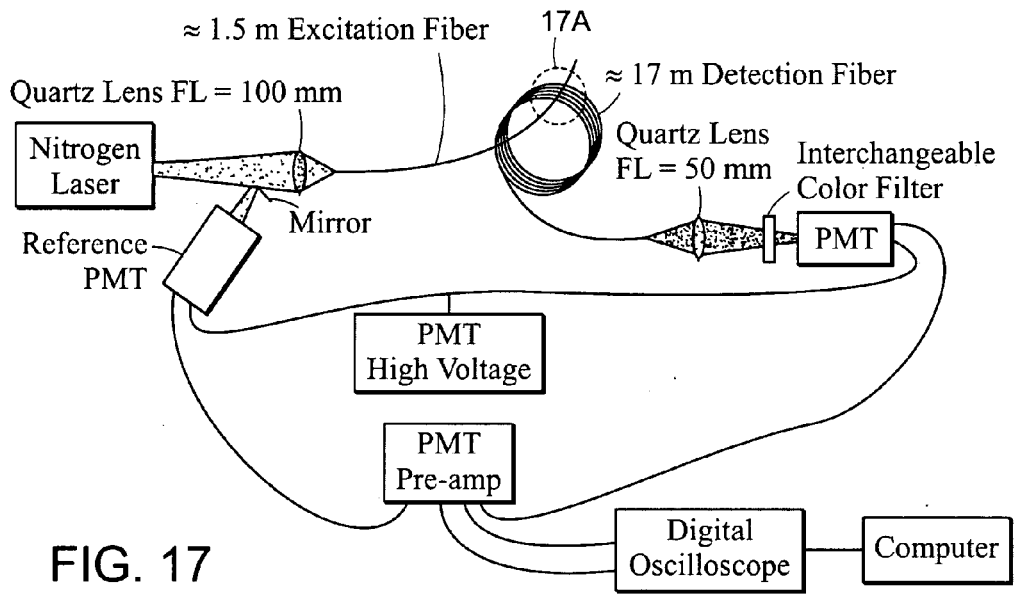
FIG. 17 shows an experimental setup using the two fiber scheme.
Figure 17A:
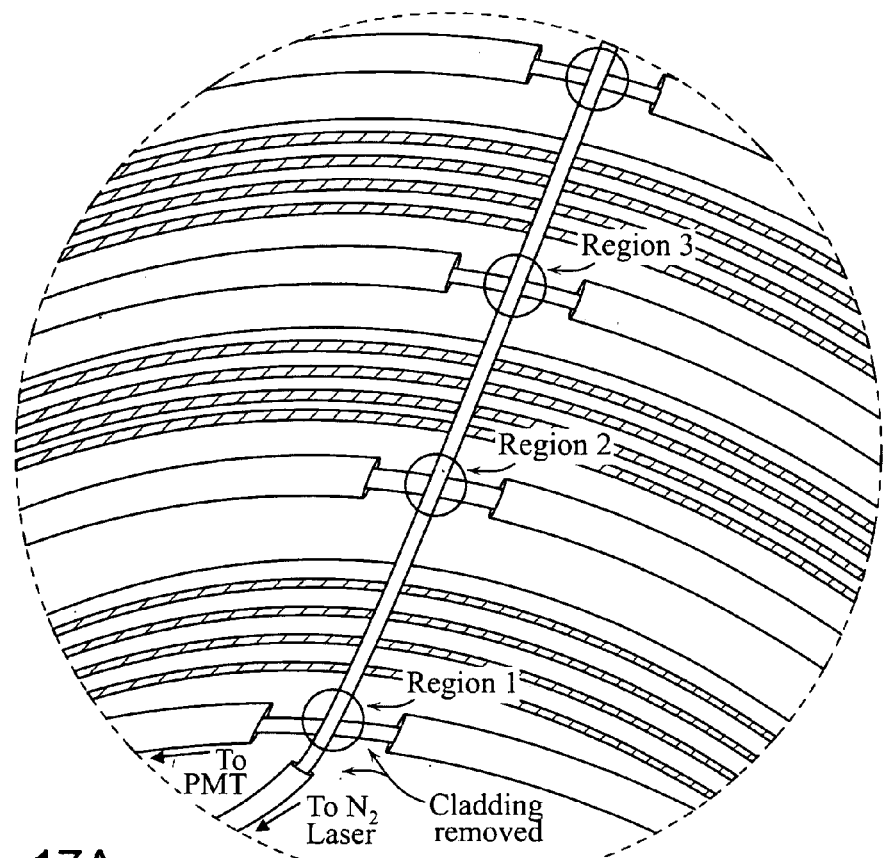

An experimental setup using the two fiber scheme as described supra is shown in FIG. 17. Two optical fibers were provided—a detection fiber, which is coiled around a cylinder, and an excitation fiber. Both fibers were multimode with 400 µm diameter silica cores (3M/Thorlabs FT-400-UMT). The TECS cladding was removed with acetone at certain regions along the fiber. The coiled detection fiber was stripped of the buffer and the cladding for a length of about 1 cm every 3.26 m. The separation of 3.26 m between adjacent regions was chosen such that the exposed core regions could be lined up parallel to the axis of the cylinder. The excitation fiber, whose buffer and cladding were also removed, was brought into direct contact with all of the exposed cores of the detection fiber. A total of six fiber-fiber connections were created.

Solutions of fluorophores were put on the fiber-fiber contacts. The regions were coated as follows:

Region 1 was coated with paraffin wax. Paraffin is a mixture of saturated hydrocarbons, with carbon backbones ranging roughly from $C_{18}$ to $C_{36}$. Moreover, paraffin exhibits fluorescence in the blue spectral regions due to the presence of polyaromatic hydrocarbons. This optical characteristic of paraffin was exploited in the experiment. Paraffin also has a refractive index that is larger than that of the removed cladding, which means that certain incident angles of light in the fiber core will couple refractivity into the paraffin. This case, which was also described in detail above, tests the recoupling efficiency from the fluorescence emitted in the paraffin host into the detection fiber.

Region 2 was coated with fluorescein in an aqueous 2% agarose solution. The refractive index of agarose is significantly smaller than that of the removed TECS cladding. In this case, the coupling from the excitation fiber to the agarose and from the agarose back into the detection fiber is purely evanescent.

Region 3 was coated with rhodamine 6G in an aqueous 2% agarose solution plus paraffin wax. This combination provided a means of testing how well fluorophores emitting at different wavelengths can be distinguished using the current experimental configuration.

Region 4 was coated with fluorescein in an aqueous 2% agarose solution. Region 4 is the same as region 2.

Region 5 was left unoccupied with no coating.

Region 6 was coated with fluorescein in an aqueous 2% agarose solution. Region 6 is the same as regions 2 and 4.

Laser pulses from a nitrogen laser (wavelength $\lambda=337.1$ nm; pulse width $\Delta t=0.6$ ns; pulse energy $E \approx 1$ mJ) were coupled into the excitation fiber with a lens matching the numerical aperture of 0.39 of the fiber. Before entering the fiber, a small fraction of the laser pulse was sent to a photodetector to provide a triggering signal for the fast oscilloscope. The laser pulse propagates through the excitation fiber reaching the fiber-fiber contacts in succession. The time separation between the excitation of adjacent regions was roughly 150 ps. The fluorophores contained in the coatings/solutions of each regions were subsequently excited. The emission was captured in the detection fiber. Since the regions along the detection fiber were spaced by 3.26 m, the fluorescence signals reaching the photomultiplier tube at the end of the detection fiber were separated by about 16 ns. In order to distinguish the emission of different fluorophores, the signal pulses were passed through various filters (band-pass or long-pass).

The output signal from the photomultiplier tube (Burle/RCA 1P28, rise time 0.78 ns) was fed through a preamplifier (Stanford Research Systems SRS445, band with 300 MHZ) to a 300 MHz digitizing oscilloscope (Hewlett Packard HP54505B). The oscilloscope was connected to a computer.

Figure 18:
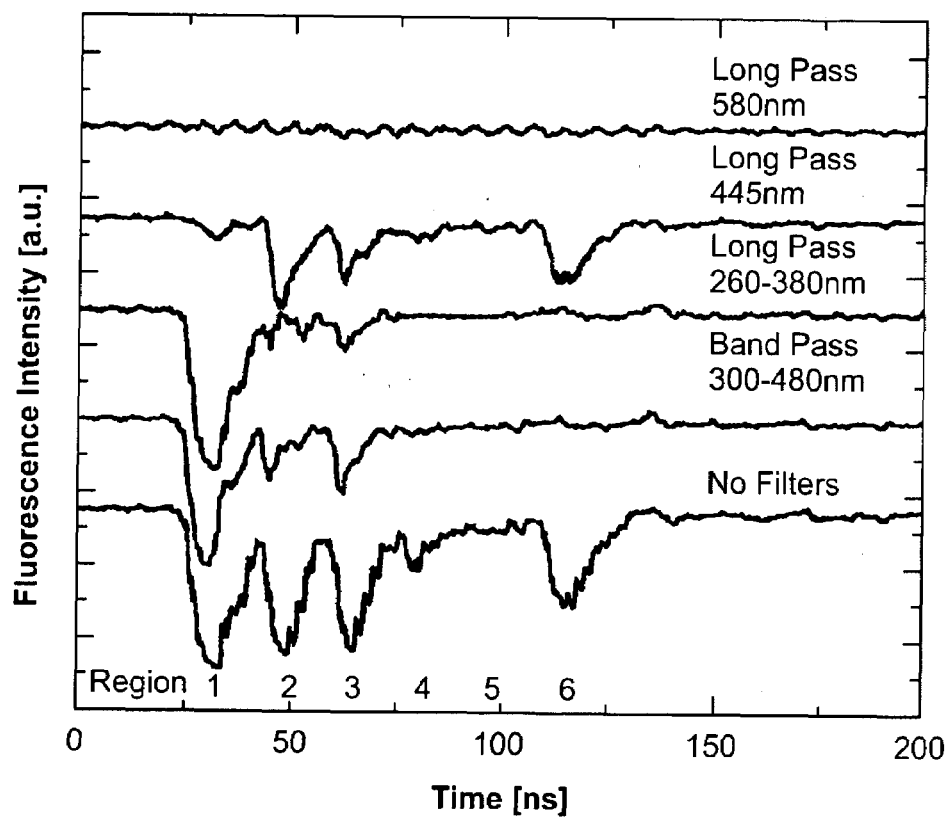
FIG. 18 shows the fluorescence signals detected through the optical fiber. Each curve of the five curves was obtained using a different filter.

FIG. 18 shows the results of the experiments for five different filter settings. All curves represent single transients (i.e., the recorded fluorescence signals are due to one single excitation laser pulse). With one pulse, the signal/noise ratio is remarkable, and the signal/noise ratio can be dramatically improved by averaging a large number of signal traces from many laser pulses. The high signal/noise ratio indicates that large arrays of sensors along a fiber are indeed quite feasible.

The bottom trace in FIG. 18 shows the signals when no filters were used in front of the photomultiplier tube. Therefore, the photomultiplier tube detected all wavelengths within its spectral response curve (200-660 nm). Indeed, five peaks, corresponding to each of the five coated regions, were detected. The uncoated region 5, as expected, produced no signal. Inserting band-pass filters that allow only light of the blue spectral region to reach the photomultiplier tuber (two cases are presented, one for a band pass of 260-380 nm and one for a band pass of 300-480 nm) left the first peak unaltered. This was expected since it is due to the paraffin fluorescence, which is in the spectral region of the pass band. The other peaks were weakened according to the specific transmission curves of the two band pass filters. The fluorescein peak of region 6 disappeared, while from region 3 only the paraffin contribution was left. The Rhodamine 6G signal from region 2 started to appear when the band pass filter 300-480 nm was used. This peak appeared strongly for the long pass filter that transmits all wavelengths above 445 nm. This filter suppressed effectively the paraffin fluorescence and the paraffin contribution to the return signal of region 3. When this long pass filter was used, the fluorescein emission from region 6 was again clearly visible. Lastly, using a long-pass filter that transmits wavelength above 580 nm resulted in no signal. The emission wavelengths of all fluorophores used were blocked by this filter.

No signal conditioning was used in acquiring the data shown in FIG. 18. Exploiting signal conditioning techniques would dramatically enhance the already high signal/noise ratio and allow for higher detection sensitivities. Also, by simply using color filters different fluorophores in the same region (e.g., region 3) can be easily distinguished. Passing the emitted light through a monochromator should also enhance the discrimination of different emitting species.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A chemical testing apparatus comprising:
   an optical fiber providing a linear support conducting light along a length between two ends; and
   a combinatorial library of probe compounds attached at discrete locations along the length of the optical fiber in a predetermined pattern, the probe compounds positioned to be exposed to target compounds applied to the optical fiber.

2. The chemical testing apparatus of claim 1 wherein the probe compounds are peptides.

3. The chemical testing apparatus of claim 1 further including a light source providing light conducted along the optical fiber to detect modification of the probe compounds during reaction with the target compounds.

4. The chemical testing apparatus of claim 3 wherein the light source is attached to at least one end of the optical fiber to transmit light by internal reflection along the length of the optical fiber to interact with multiple different probe compounds.

5. The chemical testing apparatus of claim 1 wherein the probe compounds are placed on the optical fiber to couple with evanescent waves through the fiber.

6. The chemical testing apparatus of claim 1 wherein the probe compounds repeat with a predetermined spatial pattern.

7. The chemical testing apparatus of claim 1 further including a light sensor receiving light from the optical fiber to distinguish among light interacting with different probe compounds.

8. The chemical testing apparatus of claim 7 further including a means for Fourier analysis of light received from the light sensor.

9. A method of testing an analyte having target compounds, the method comprising the steps of:
   (a) preparing an optical fiber with a combinatorial library of probe compounds attached at discrete locations along the length of the optical fiber in a predetermined pattern;
   (b) exposing the prepared optical fiber to target compounds in an analyte; and
   (c) photometrically analyzing the exposed and prepared optical fibers to detect reaction of the probe compounds with the target compounds from the analyte.

10. The method of claim 9 wherein the probe compounds are peptides.

11. The method of claim 9 further wherein the step of analyzing conducts light along the optical fiber to detect modification of the probe compounds during reaction with the target compounds.

12. The method of claim 11 wherein the light source is attached to at least one end of the optical fiber to transmit light by internal reflection along the length of the optical fiber, whereby light from the light source is capable of interacting with multiple different probe molecules.

13. The method of claim 9 wherein the probe compounds are placed on the optical fiber to couple with evanescent waves through the fiber.

14. The method of claim 9 wherein the probe molecules repeat with a predetermined spatial pattern.

15. The method of claim 9 further including the step of receiving light conducted along the optical fiber at a light sensor capable of distinguishing among light that has interacted with different probe molecules.

16. The method of claim 15 further including the step of conducting a Fourier analysis of the light received by the light sensor.

* * * * *

UNITED STATES PATENT AND TRADEMARK OFFICE
CERTIFICATE OF CORRECTION

| | | |
|---|---|---|
| PATENT NO. | : 7,244,572 B1 | Page 1 of 1 |
| APPLICATION NO. | : 09/535300 | |
| DATED | : July 17, 2007 | |
| INVENTOR(S) | : Alan W. Schwabacher et al. | |

It is certified that error appears in the above-identified patent and that said Letters Patent is hereby corrected as shown below:

In the Specification

Column 1, line 6

Replace:
[[The work described herein was supported, in part, by grants from the National Science Foundation (CHE-9726030). The United State government may have certain rights in the invention.]]

with:
---This invention was made with government support under CHE-9726030 awarded by the National Science Foundation. The government has certain rights in the invention.---

Signed and Sealed this
Thirty-first Day of March, 2015

Michelle K. Lee
*Director of the United States Patent and Trademark Office*